(12) United States Patent
Tagg et al.

(10) Patent No.: US 7,595,041 B2
(45) Date of Patent: Sep. 29, 2009

(54) TREATMENT OF MALODOUR

(75) Inventors: John Robert Tagg, Dunedin (NZ);
Christopher Norman Chilcott, Dunedin (NZ); Jeremy Paul Burton, Dunedin (NZ)

(73) Assignee: BLIS Technologies Limited, Dunedin (NZ)

( * ) Notice: Subject to any disclaimer, the term of this patent is extended or adjusted under 35 U.S.C. 154(b) by 323 days.

(21) Appl. No.: 10/564,799

(22) PCT Filed: Jul. 19, 2004

(86) PCT No.: PCT/NZ2004/000153

§ 371 (c)(1),
(2), (4) Date: Jan. 13, 2006

(87) PCT Pub. No.: WO2005/007178

PCT Pub. Date: Jan. 27, 2005

(65) Prior Publication Data

US 2006/0171901 A1 Aug. 3, 2006

(30) Foreign Application Priority Data

Jul. 18, 2003 (NZ) ..................................... 527075
Apr. 20, 2004 (NZ) ..................................... 532382

(51) Int. Cl.
*A61K 35/74* (2006.01)
*A01N 63/00* (2006.01)

(52) U.S. Cl. ................................... 424/93.44; 424/780

(58) Field of Classification Search ....................... None
See application file for complete search history.

(56) References Cited

U.S. PATENT DOCUMENTS 5,672,351 A * 9/1997 Chikindas et al. ........... 424/401
5,772,986 A * 6/1998 Kross .......................... 424/53
6,350,438 B1 * 2/2002 Witt et al. ..................... 424/53
6,773,912 B1 * 8/2004 Tagg et al. ................ 435/253.4
2001/0043941 A1* 11/2001 Huatan et al. ............... 424/442

FOREIGN PATENT DOCUMENTS

| WO | WO01/27143 | * | 4/2001 |
| WO | WO 03/070919 A1 | | 8/2003 |
| WO | WO 2004/072272 | | 8/2004 |

OTHER PUBLICATIONS

Bosy et al, *Replationship of Oral Malodor to Periodontitis: Evidence of Independence in Discrete Subpopulations*, Oral Maldor and Periodontis, vol. 65, No. 1, Jan. 1994, pp. 37-46
Burton et al, Evaluation of the Bacterial Vaginal Flora of 20 Postmenopausal women by Direct (Nugent Score) and Molecular (Polymerase Chain Reaction and Denaturing gradient Gel Electrophoresis) Techniques, The Journal of Infectious Diseases, Dec. 2002, 186: pp. 1770-1780.
De Boever et al, assessing the Contribution of Anaerobic Microflora of the Tongue to Oral Malodor, JADA, vol. 126, Oct. 1995, pp. 1384-1393.
Kazor et al, Diversity of Bacterial Populations on the Tongue Dorsa of Patients with Halitosis and Healthy Patients, Journal of Clinical Microbiology, Feb. 2003, vol. 41, No. 2, pp. 558-563.
Tagg et al, "Fingerprinting" β-*Haemolytic streptococci* by their Production of and Sensitivity to Bacteriocine-Like Inhibitors, The Journal of Medical Microbiology, vol. 12, No. 4, Aug. 7, 1978, pp. 397-411.
Walter et al, "Detection and Identification of Gastrointestinal *Lactobacillus* Species by Using Denaturing Gradient gel Electrophoresis and Species-Specific PCR Primers", Applied and Environmental Microbiology, vol. 66, No. 1, Jan. 2000, pp. 297-303.
Yaegaki et al, Examination, Classification, and Treatment of Halitosis; Clinical Perspectives, J Can Dent Assoc 2000, vol. 66, pp. 257-261.

* cited by examiner

*Primary Examiner*—Christopher R. Tate
(74) *Attorney, Agent, or Firm*—Frommer Lawrence & Haug LLP

(57) ABSTRACT

This invention relates to methods for inhibiting growth of anaerobic bacteria, particularly halitosis causing bacteria. The methods use BLIS-producing *Streptococcus salivarius* strains, extracts thereof, and compositions comprising same in the prevention or treatment of halitosis.

27 Claims, 2 Drawing Sheets

TREATMENT OF MALODOUR

CROSS REFERENCE TO RELATED APPLICATIONS

This application is the U.S. national phase application under 35 U.S.C. § 371 of International Application No. PCT/NZ2004/000153, filed Jul. 19, 2004, published as WO 2005/007178 on Jan. 27, 2005, and claiming priority to New Zealand Application No. 527075, filed Jul. 18, 2003 and New Zealand Application No. 532382, filed Apr. 20, 2004.

FIELD OF THE INVENTION

This invention relates to methods of inhibiting growth of anaerobic bacteria, particularly halitosis causing bacteria, and to the use of BLIS-producing *Streptococcus salivarius* strains, extracts thereof, and compositions containing same in the prevention or treatment of halitosis.

BACKGROUND

Halitosis or bad breath is a common complaint characterised at least in part by the production of volatile sulfur compounds. The production of such compounds is generally associated with oral bacteria, particularly certain anaerobic species. These bacteria generally inhabit oral surfaces, and particularly periodontal pockets and the dorsa of the tongue surface.

The primary source of volatile sulphur compounds (VSC's) from the subgingival microflora is from microorganisms that can be both commensal and pathogenic. Previous culture-based studies have indicated that *Porphyromonas gingivalis*, *Prevotella intermedia* (both black pigmented species, *Fusobacterium nucleatum*, *Micromonas micros* (formerly, *Peptostreptococcus*), *Bacteroides* species, *Campylobacter rectus*, *Eikenella corrodens*, *Desulfovibrio* species, *Treponema denticola*, and *Eubacterium* species amongst others are responsible for the production of VSC's that contribute to halitosis (as summarized by Loesche W J, Kazor C. Periodontol 2000. 2002; 28:256-79. and Khaira N, Palmer R M, Wilson R F, Scott D A, Wade W G. Oral Dis. 2000 November; 6 (6):371-5.). However, recent non-culture based studies have shown that there are certain species associated with subjects that are either healthy or afflicted with halitosis. *Atopobium pavulum*, *Eubacterium sulci*, *Fusobacterium periodonticum*, *Dialister*, a phylotype of streptococci, a phylotype of the uncultivated phylum TM7, and *Solobacterium moorei* appeared to be present in subjects with halitosis. By contrast, *Streptococcus salivarius*, *Rothia mucilaginosa* (*Stomatococcus mucilaginosus*), and an uncharacterized *Eubacterium* (strain FTB41) were commonly detected only amongst healthy individuals (Kazor, C. E. et al., J. Clin Microbiol, February 2003, pp 558-563).

Over the years various methods have been developed and tried with varying success, to prevent or at least alleviate the problem of halitosis. Current treatments focus on anti bacterial regimes to reduce numbers of oral bacteria, or agents to mask or neutralise the offensive odour. Oral rinses with chlorine dioxide (see for example, WO 95/27472 and U.S. Pat. No. 5,738,840) have been shown to have some effect in the control of halitosis, but offer only temporary relief in the order of a few days. Generally, current methods of treating halitosis require complex physical, chemical or expensive regimes to be carried out and are typically only of short term effect, as the malodour-causing oral bacteria recover to former levels after treatment is stopped.

What is sought to treat halitosis is the replacement of the disease-causing organisms, with a non-virulent commensal microorganism. To serve as an effector strain in replacement therapy, the microorganism must be able to compete successfully with the pathogenic microorganism either via competitive action (e.g. for attachment sites), and/or antibiotic action, or inhibition by other metabolism-associated by-products.

In WO 01/27143 *S. salivarius* strains are identified which have utility in the treatment of infections of the upper respiratory tract caused by streptococcal organisms, including treatment of sore throats caused mainly by *S. pyogenes*, and dental caries caused at least in part by *S. sobrinus*. No activity was recorded against any anaerobic microorganisms. Moreover, the treatment of halitosis is nowhere contemplated in that document.

The present invention is broadly directed to methods of at least inhibiting growth of anaerobic microorganisms using BLIS-producing *S. salivarius* strains or compositions comprising same, or at least provides the public with a useful choice.

SUMMARY OF THE INVENTION

Accordingly, in one aspect the invention provides a method for at least inhibiting the growth of anaerobic bacteria sensitive to BLIS-producing *S. salivarius*, the method comprising contacting the sensitive bacteria with an inhibitory effective amount of a BLIS-producing *S. salivarius*, or an extract thereof, or a composition comprising said *S. salivarius* or extract thereof.

In a further aspect, the invention provides a method of prophylactic or therapeutic treatment of halitosis in an individual in need thereof, the method comprising administering to said individual a BLIS-producing *S. salivarius*, extract thereof, or composition comprising said *S. salivarius* or extract thereof, in an amount effective to at least inhibit growth of anaerobic bacteria, or in an amount to allow effective colonisation in the oral cavity of the individual by BLIS-producing *S. salivarius*.

Preferably the *S. salivarius* are Salivaricin B producers.

Commonly, the anaerobic bacteria are black pigmented species, and/or *Eubacterium* and/or *Micromonas*, especially *Prevotella* species, *Eubacterium saburreum* and *Micromonas micros*.

In a further aspect, the invention provides a method of controlling the incidence and/or severity of halitosis, the method comprising introducing into the oral cavity of an individual susceptible to halitosis an amount of a BLIS-producing *S. salivarius*, extract thereof, or composition comprising said *S. salivarius* or extract thereof, effective to control the incidence or severity of said halitosis.

In one embodiment the halitosis is caused at least in part by one or more black pigmented species, *Eubacterium* and/or *Micromonas*, particularly *Prevotella* species, *Eubacterium saburreum* and *Micromonas micros*.

Preferably, *S. salivarius* is administered as part of a lozenge, spray, mouth rinse, or other drug delivery device, confectionary (including chewing gum), food, drink or nutraceutical.

The methods of the invention preferably include the preliminary step of pre-treating the individual to at least reduce the oral microflora already present.

The invention also relates to the use of BLIS-producing *S. salivarius*, extracts thereof, or compositions comprising same in the methods discussed above. Particularly, to the use of the *S. salivarius* in the preparation of medicaments for use in treating halitosis.

In another aspect, the invention also relates to the use of BLIS-producing *S. salivarius*, extracts thereof, and compositions comprising said *S. salivarius* or extracts thereof in the methods discussed above for inhibiting, controlling, preventing or treating halitosis caused at least in part by one or more *Prevotella* species and/or *Eubacterium saburreum* and/or *Micromonas micros*.

The invention also provides a method of prophylactic or therapeutic treatment of halitosis in an individual in need thereof, the method comprising administering to said individual a BLIS-producing *S. salivarius*, extract thereof, or composition comprising said *S. salivarius* or extract thereof, effective to at least inhibit growth of anaerobic bacteria, or in an amount to allow effective colonisation in the oral cavity of the individual by BLIS-producing *S. salivarius*.

Although the invention is broadly as described above, it will be appreciated by those persons skilled in the art that the invention is not limited thereto but also includes embodiments of which the following description gives examples. In particular, the invention will be described in relation to the accompanying drawings.

DETAILED DESCRIPTION OF THE INVENTION

Figure 1:
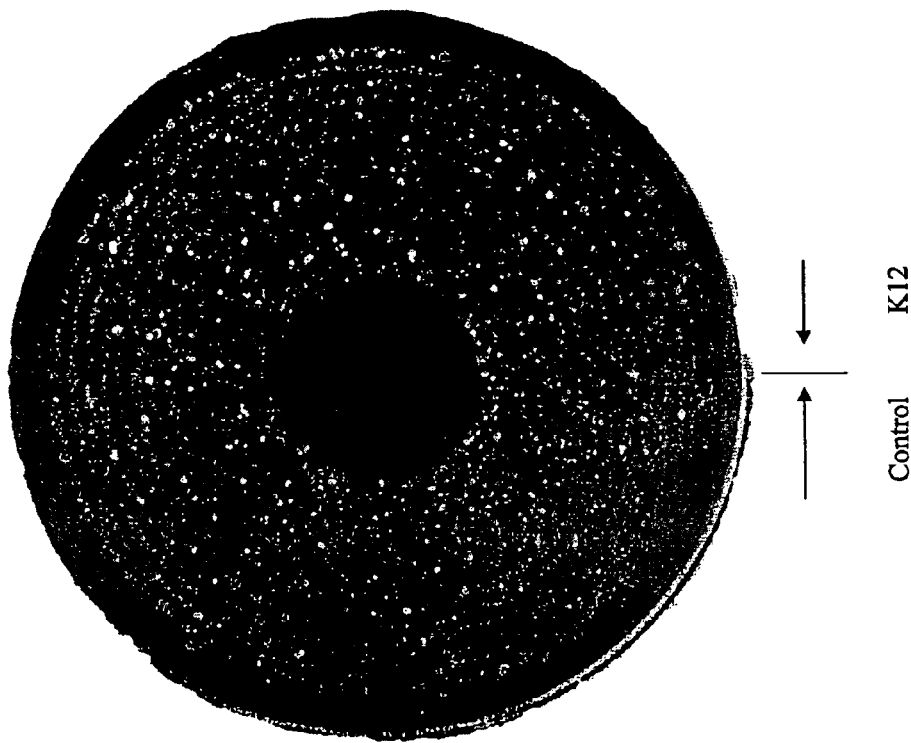
FIG. 1. Example of inhibitory effect of *S. salivarius* K12 on black-pigmented bacteria (*Prevotella* species) from saliva sample.
Figure 2A:
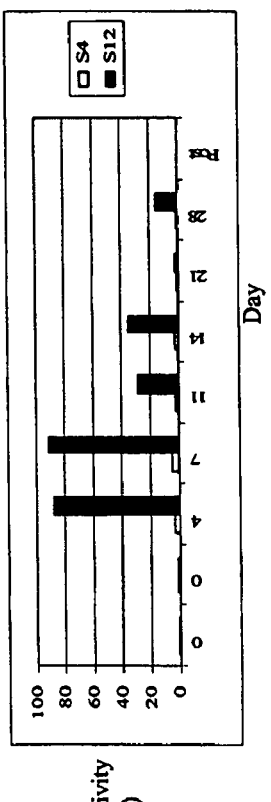
FIG. 2A. Bar graph showing VSC levels of mouth air from two case subjects (4 and 12) over 28 days and after treatment.
Figure 2B:
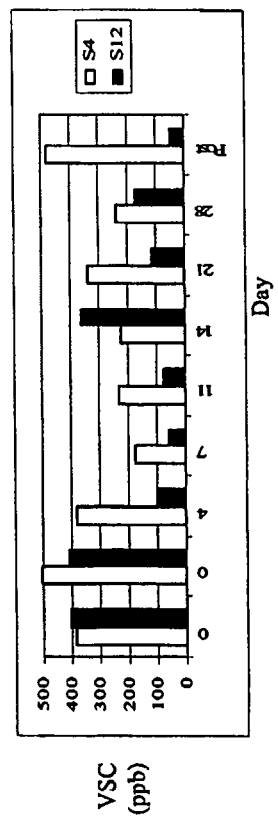
FIG. 2B. Bar graph showing detection of BLIS activity of *Streptococcus salivarius* isolates (%) from case subjects over time by sensitive indicator microorganism *Micrococcus leuteus* (I1, sensitive to SAL A and B).
Figure 2C:
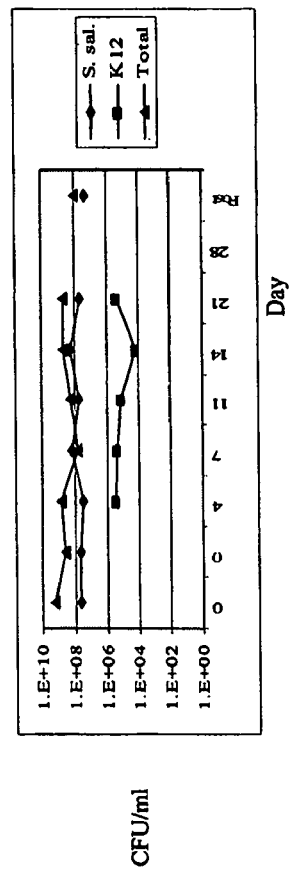
FIG. 2C. Bacterial counts of saliva from subject 4.
Figure 2D:
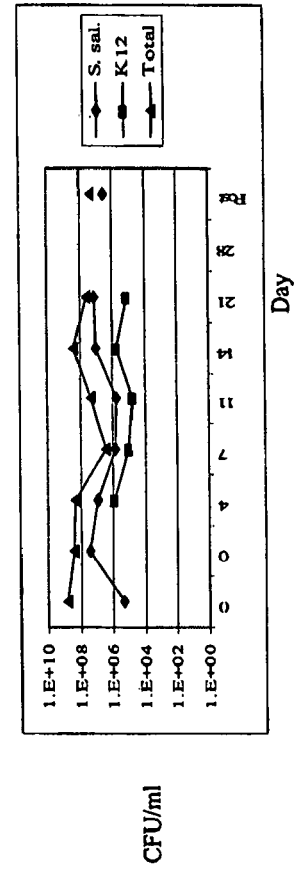
FIG. 2D. Bacterial counts of saliva from subject 12.

As noted above, the present invention is directed in a first aspect to a method for at least inhibiting the growth of anaerobic bacteria sensitive to BLIS-producing *S. salivarius*. The method comprises contacting the sensitive bacteria with an inhibitory effective amount of a BLIS-producing *S. salivarius*, or an extract thereof, or a composition containing the *S. salivarius* or extract thereof.

The phrase "inhibiting the growth of anaerobic bacteria sensitive to BLIS-producing *S. salivarius*" as used herein refers to the growth inhibition of at least one strain of one or more species of anaerobic bacteria sensitive to BLIS-producing *S. salivarius*. Inhibition of growth may be determined by deferred antagonism tests on agar as described by Tagg and Banister (J. Med. Microbiol. 1979; 12: 397) as illustrated in the accompanying examples.

The term "contacting" as used herein refers to both direct and indirect contact between the anaerobic bacteria and a BLIS-producing *S. salivarius*, extract, or composition herein. Indirect contact comprises exposure of the anaerobic bacteria in its native environment, particularly native environment, to a BLIS-producing *S. salivarius*, extract, or composition herein.

The anaerobic bacteria to be treated are preferably in the oral cavity of an individual.

In another embodiment the invention therefor relates to methods of prophylactially or therapeutically treating halitosis, and to methods of controlling the incidence and severity of halitosis as set out above.

Preferably, the *S. salivarius* strains for use in the invention are native Salivaricin B producers with activity against anaerobic bacteria, particularly black pigmented species (such as *Prevotella*), *Eubacterium saburreum* and/or *Micromonas micros*. Salivaricin B BLIS-producing strains with activity against anaerobic bacteria include K12, and K30 both deposited under the Budapest Treaty with Deutche Sammlung von Mikroogranismen Und Zeflkulturen GmbH, Mascheroder Weg 1 b, D-38124, Braunschweig, Germany on 8 Oct. 1999, and 8 Oct. 1999, and assigned Accession Nos. DSM 13084 and 13085 respectively.

Strain Sal 20P3 was deposited at the Australian Government Analytical Laboratories, 1 Suakin Street, Pymble, New South Wales, Australia in July 1992 under Accession No. AGAL 92/32401.

Sal 20P3 is a producer of Salivaricin A only and has activity against at least *Micromonas*. Salivaricin B producers K12 and K30 have a broader range of activity against black pigmented species, *Eubacterium* and *Micromonas* at least.

*S. salivarius* BLIS-producers may be identified by testing potential producer strains in agar surface assays as taught in WO 01/27143. Production of Salivaricin A, $A_2$ and B may be confirmed by comparing sequence identity and activity to those sequences and activity data given in WO 01/27143. For convenience, the amino acid sequences of Salivaricins useful in the invention are as follows:

| Salivaricin | Amino Acid and Nucleic Acid Sequence |
|---|---|
| A | MKNSKDILNNAIEEVSEKELMEVAGG<br>-1<br>KRGSGWIATITDDCPNSVFVCC (SEQ ID NO:1)<br>+1<br>ATGAATGCCATGAAAAACTCAAAAGATATTTTGAACAATGCTATCGAAGAAGTTTCTGA<br>AAAAGAACTTATGGAAGTAGCTGGTGGTAAAAGAGGTTCAGGTTGGATTGCAACTATTA<br>CTGATGACTGTCCAAACTCAGTATTCGTTTGTTGTTAA (SEQ ID NO:2) |
| $A_1$ | MKNSKDILTNAIEEVSEKELMEVAGG<br>-1<br>KKGSGWFATITDDCPNSVFVCC (SEQ ID NO:3)<br>+1<br>ATGAGTTTTATGAAAAATTCAAAGGATATTTTGACTAATGCTATCGAAGAAGTTTCT<br>GAAAAAGAACTTATGGAAGTAGCTGGTGGTAAAAAAGGTTCAGGTTGGTTTGCAACT<br>ATTACTGATGACTGTCCGAACTCAGTATTTGTTTGTTGTTAA (SEQ ID NO:4) |

-continued

| Salivaricin | Amino Acid and Nucleic Acid Sequence |
|---|---|
| A₂ | atg att gcc atg aaa aac tca aaa gat att ttg aac aat<br>Met Ile Ala Met Lys Asn Ser Lys Asp Ile Leu Asn Asn<br><br>gct atc gaa gaa gtt tct gaa aaa gaa ctt atg gaa gta<br>Ala Ile Glu Glu Val Ser Glu Lys Glu Leu Met Glu Val<br><br>gct ggt ggt aaa aga ggt aca ggt tgg ttt gca act att<br>Ala Gly Gly Lys Arg Gly Thr Gly Trp Phe Ala Thr Ile<br>           -1  +1<br><br>act gat gac tgt cca aac tca gta ttc gtt tgt tgt taa (SEQ ID NO:5)<br>Thr Asp Asp Cys Pro Asn Ser Val Phe Val Cys Cys (SEQ ID NO:6) |
| B | ttg act ctt gaa gaa ctt gat aac gtt ctt ggt gct ggt<br>Leu Thr Leu Glu Glu Leu Asp Asn Val Leu Gly Ala Gly<br>                                                  -1 +1<br><br>ggt gga gta atc caa acc att tca cac gaa tgt cgt atg<br>Gly Gly Val Ile Gln Thr Ile Ser His Glu Cys Arg Met<br><br>aac tca tgg cag ttc ttg ttt act tgt tgc tct taa (SEQ ID NO:7)<br>Asn Ser Trp Gln Phe Leu Phe Thr Cys Cys Ser (SEQ ID NO:8) |

The sequence for Salivaricin A₁ is also given as a further BLIS useful in the invention.

Sequence comparison may be achieved using BLASTP.

More particularly, polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp://ftp.ncbi.nih.gov/blast/). The default parameters of bl2seq may be utilized.

Polypeptide sequence identity may also be calculated over the entire length of the overlap between a candidate and subject polynucleotide sequences using global sequence alignment programs. EMBOSS-needle (available at the website of the European Bioinformatics Institute) and GAP (Huang, X. (1994) On Global Sequence Alignment. Computer Applications in the Biosciences 10, 227-235) are also suitable global sequence alignment programs for calculating polypeptide sequence identity.

Use of BLASTP as described above is preferred for use in the determination of polypeptide variants useful in the present invention.

As noted above black pigmented species, *Eubacterium* and *Micromonas* are considered causative agents in halitosis. While the BLIS-producing strains of *S. salivarius* above are known to be active against gram-positive aerobic bacteria, their activity against anaerobic bacteria, such as black pigmented species, *Eubacterium* and *Micromonas* in particular, is unexpected. All the more so because BLIS-producing organisms are typically known to act against more closely related species.

These BLIS-producing *S. salivarius* are therefore useful as anaerobic antibacterial agents per se as well as therapeutically. In this context, "therapeutic" includes prophylactic treatment. Therapeutic uses include the treatment or prevention of anaerobic microbial infections, especially *Eubacterium* and *Micromonas* infections, and infections by black pigmented species. The *S. salivarius* are particularly suitable for use against *Prevotella* species including *P. intermedia* and *P. melaninogenica; Eubacterium saburreum, Micromonas micros, Streptococcus anginosus,* some or all of which may be implicated in halitosis. Conditions amenable to treatment with the *S. salivarius* strains include halitosis (or bad breath).

Extracts obtainable from the BLIS-producing salivarius strains are also useful in the invention. Extracts include those in which the BLIS or BLIS' produced by the salivarius strain is/are provided in isolated or pure form. An "isolated" BLIS is one which has been identified and separated and/or recovered from its natural cellular environment. Extracts can be obtained using known art protocols, conveniently by cell culture and centrifugation. Routine isolation methods include ammonium sulphate precipitation, column chromatography (e.g. ion exchange, gel filtration, affinity chromatography etc.), electrophoresis, and ultimately, crystallisation (see generally "Enzyme Purification and Related Techniques". *Methods in Enzymology,* 22: 233-577 (1991)). The BLIS may be purified as necessary using conventional techniques (see for example, Parente, E and Ricciardi, A. Applied Microbiol. Biotechnol 52: 628 (1999)).

The BLIS may be purified to greater than 95% by weight of BLIS as determined by the Lowry method (Lowry, O. H. et al., 1951. Protein Measurement with Folin-Phenol Reagents. *J. Biol. Chem.* 193: 265-275). Preferably the BLIS will be purified to 99% or more by weight.

These active extracts may similarly be used in therapeutic formulations and methods. Extracts include the BLIS antibiotics salivaricin A, A₁, A₂ and B or variants thereof in isolated or pure form. The variants are functionally equivalent in that they exhibit similar antibiotic properties to salivaricin A, A₁, A₂ and B. The antibiotics and variants together with processes for their production are taught in WO 01/27143 incorporated herein by reference. The term "variant" of the antibiotic polypeptides encompasses naturally occurring, recombinantly and synthetically produced polypeptides.

Variant polynucleotide and polypeptide sequences refer to polynucleotide or polypeptide sequences different from the specifically identified BLIS antibiotic sequences, wherein one or more nucleotides or amino acid residues is deleted, substituted or added. Variants may be naturally occurring allelic variants, or non-naturally occurring variants. Variants may be from the same or other species and encompasses homologues, paralogues and orthologues. Both cDNA and genomic sequence variants are contemplated. Variant sequences preferably exhibit at least 70%, preferably at least 80%, more preferably at least 90%, more preferably at least 95%, more preferably at least 98%, and most preferably at least 99% identity to a BLIS sequence useful in the present invention. For polypeptides, identity is found over a comparison window of at least 15, preferably at least 18 amino acid positions, more preferably at least 20 amino acid positions, and most preferably over the entire length of a polypeptide.

Sequence identity may be determined as discussed above.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306) and WO 01/27143.

The antibiotics and variants useful in the invention can be prepared in a variety of ways. For example, by isolation from a natural source (such as *S. salivarius* strains K12 and/or K30), by synthesis using any suitable known techniques (such as is described for nisin synthesis by Wakamiya et al., (1991) in "Nisin and Novel Lantibiotics" ed. G. Jung and H. G Shal, 189-203, Escom, Leiden or by solid phase synthesis as described by Merrifield (1964) *J. Am. Chem. Assoc.* 85, 2149-2154, or by synthesis in homogeneous solution as described by Houbenwycl (1987), Methods of Organic Chemistry, Vol I and II) or through employing recombinant DNA techniques such as described by Sambrook et al (1989), Molecular cloning: A Laboratory Manual, Cold Spring Harbour Press, New York, USA.

The variants of both the native BLIS and its variants can similarly be made by any of those techniques known in the art. For example, variants can be prepared by site-specific mutagenesis of the DNA encoding the native amino acid sequence as described by Adelman et al., DNA 2, 183 (1983).

The variant sequences, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673 -4680, see the website of the European Molecular Biology Laboratory) or T-COFFEE (Cedric Notredame, Desmond G. Higgins, Jaap Heringa, T-Coffee: A novel method for fast and accurate multiple sequence alignment, J. Mol. Biol. (2000) 302: 205-217))or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (accessible on the Swiss Institute of Bioinformatics website) contains biologically significant patterns and profiles and is designed so that it can be used with appropriate computational tools to assign a new sequence to a known family of proteins or to determine which known domain(s) are present in the sequence (Falquet et a!., 2002, Nucleic Acids Res. 30, 235). Prosearch is a tool that can search SWISS-PROT and EMBL databases with a given sequence pattern or signature.

In addition to the computer/database methods described above, polypeptide variants may be identified by physical methods, for example by screening expression libraries using antibodies raised against antibiotic polypeptides used in the invention (Sambrook et al., Molecular Cloning: A Laboratory Manual, 2nd Ed. Cold Spring Harbor Press, 1987) or by identifying polypeptides from natural sources with the aid of such antibodies.

Variant polynucleotides useful herein also or alternately hybridize to the polynucleotide sequences recited above, or complements thereof, antisense sequences and complements thereof, under stringent conditions. As used herein, "stringent conditions" refers to hybridization conditions such as prewashing in a solution of 6×SSC, 0.2% SDS; hybridizing at 65° C., 6×SSC, 0.2 SDS overnight; followed by two washes of 30 minutes each in 1×SSC, 0.1% SDS at 65° C. and two washes of 30 minutes each in 0.2×SSC, 0.1% SDS at 65° C. Such conditions are discussed more fully in, for example, Sambrook et al., Molecular supra.

Recombinant production of a BLIS useful in the invention can be achieved using well known art techniques as taught in WO 01/27143.

A "therapeutic composition" is a composition appropriate for administration of a S. salivarius strain or extract herein, to an individual in need of same, particularly a halitosis-susceptible individual. In general, therapeutic compositions are composed of a S. salivarius strain or extract discussed above and an acceptable carrier, diluent and/or excipient.

An "acceptable carrier, diluent and/or excipient" means a vehicle for delivery of a S. salivarius strain or extract, to the individual, in which the vehicle is compatible with bacterial cell viability, or activity of the extract. Acceptable carriers, diluents and excipients suitable for use in the administration of viable S. salivarius strains and extracts are well known to those skilled in the art (see, for example, Remington's Pharmaceutical Sciences, 18th ed., Gennaro, ed., 1990, Mack Publishing Co., Easton, Pa., incorporated herein by reference. Suitable carriers are generally inert and can be either solid or liquid.

In one embodiment, the carrier is a pharmaceutically acceptable carrier. Pharmaceutically acceptable carriers suitable for use with the S. salivarius strains herein include, but are not limited to, water, buffered saline solutions (e.g., phosphate-buffered saline), pharmaceutically acceptable culture media (e.g. BACa, TSBCaYE agar), or other solutions which maintain the viability of the bacterium. Additionally, such pharmaceutically acceptable carriers may be aqueous or non-aqueous solutions, suspensions, and emulsions. A variety of pharmaceutically acceptable carriers suitable for oral administration of viable or lyophilized bacteria are well known in the art (see, for example, Remington's supra.); and the pharmaceutical composition LACTINEX™ (Hynson, Westcott and Dunning, Baltimore, Md. USA), a commercially available formulation for oral administration of viable lactobacilli). Suitable solid carriers known in the art include, for example, magnesium carbonate; magnesium stearate; celluloses; talc; sugars such as fructose, sucrose, mannitol, lactose; starches; flours; oligosaccharides and skim milk, and similar edible powders, but are not limited thereto. Carriers for administration of extracts are similarly well known.

Typical diluents, by way of example, are: starches; lactose; mannitol; kaolin; calcium phosphate or sulphate; inorganic salts such as sodium chloride; and powdered sugars or celluloses.

The compositions may also include excipients such as tableting aids; resins; fillers; binders; lubricants; solvents; glidants; disintegrants; preservatives; buffers; flavourings; colourings; sweeteners; and fragrances as appropriate. A preferred excipient for tablet flowability and compactability is ProSolv™ (Penwest, N.Y., USA). A preferred sweetener is isomalt.

Typical binders include starch; gelatin; sugars such as lactose, fructose, and glucose; and the like. Natural and synthetic gums are also convenient, including acacia; alginates; locust bean gum; methylcellulose; polyvinylpyrrolidine tragacanth; Xanthan gum: and the like. Polyethylene glycol; ethyl cellulose; and waxes can also serve as binders. A currently preferred binder is Emdex™ (Penwest, N.Y., USA).

Lubricants to prevent sticking to the die during formation include slippery solids such as talc, silica, magnesium and calcium stearate, polyethylene glycol, stearic acid and hydrogenated vegetable oils.

Disintegrators are substances which swell when wetted to break up the composition and release the S. salivarius or extract. The disintegrators include starches; clays; celluloses; algins and gums; more particularly corn and potato starches; methylcellulose; agar; bentonite; wood cellulose; cation exchange resins; alginic acid; guar gum; citrus pulp; carboxymethylcellulose; powdered sponge; and sodium lauryl sulfate.

The S. salivarius strains or extracts herein can be formulated in any of a variety of compositions suitable for oral administration. For example, the S. salivarius strains can be formulated for administration as a lyophil or cell paste prepared from a S. salivarius culture, or can be directly administered to the oral cavity. The strain or extract can also be administered in the form of a mouthwash, mouth rinse, toothpaste, dentifrice, mouthspray, gargle, capsule, lozenge, syrup, floss, film, chewing gum, or chewable tablet but the forms are not limited thereto.

Therapeutic compositions may include food, confectionary or drink. In one embodiment, the foodstuff or drink is a dairy product-based food or drink including by way of example, yoghurt, cheese, milk, milk power, milk biscuits, and flavoured milks. In the case of confectionary, the formulation can be a chewing gum such as described in WO 00/05972. One preferred composition employs freeze dried *S. salivarius* strains herein, in milk powder formulations in a manner similar to that previously reported for the preparation of Bifidus Milk Powder (Nagawa et al. (1988); J. Dairy Sci. 71:1777-1782).

One orally administrable composition of *S. salivarius* is a blend of freeze dried *S. salivarius* strains with skim milk powder or the like which has been flavoured to enhance palatability.

Presently preferred orally administrable compositions of *S. salivarius*, or extracts herein are lozenges, chewable tablets, or capsules. Lozenges such as BLIS K12 formulations (BLIS Technologies Limited, Wellington, New Zealand) are particularly preferred. A suckable lozenge preferably comprises an *S. salivarius* strain or extract, isomalt and Emdex™. The lozenge may be prepared by direct compression, wet granulation, or dry granulation. The lozenges may be coated according to well known pharmaceutical practice.

The therapeutic composition can additionally contain nutrients to maintain the viability of the bacterium in the formulation. As noted above, the composition can also contain flavouring agents, colouring agents, fragrances, or other compounds which increase the palatability of the composition and/or enhance patient compliance without compromising the effectiveness of the composition. Methods for preparation of compositions for oral administration are well known in the art (see, for example, Remington's Pharmaceutical Sciences, 18th ed., supra, incorporated herein by reference).

For general antimicrobial use, compositions may also be produced for other methods of administration including topically administrable compositions but not limited thereto.

The compositions may further comprise one or more secondary antibacterial agents. These secondary agents may, for example, be antibiotics, or other antibacterial agent or antibacterial producing microorganisms. Preferably, the secondary antibacterial agent is a BLIS or BLIS producing microorganism. The BLIS may be one or more of salivaricin A, $A_1$, $A_2$ and B.

Secondary agents useful in such a composition may be odour masking or neutralising agents such as peppermint, chlorine dioxide, zinc, baking soda or other agents with a similar purpose.

Other ingredients useful in such a composition are anticariogenic agents, for example Xylitol, fluoride, and calcium.

Further ingredients useful in such a composition are agents that selectively enhance growth of desirable bacteria over non desirable organisms. These agents may, for example, be oligosaccharides such as Nutriose® FB (Roquette Freres, Lestrem, France).

In the treatment of halitosis, *S. salivarius* strains or extracts can be administered to any individual susceptible to halitosis, usually an individual in which black pigmented species, *Eubacterium* and/or *Micromonas* colonises the oral cavity such that the halitosis is caused at least in part by one or more black pigmented species, *Eubacterium* and/or *Micromonas*.

The term "individual" as used herein includes humans, horses, dogs, cats, pigs, sheep, cattle, goats but is not limited thereto. Preferably, the individual is a human. The *S. salivarius* strains can be administered to the individual at any age, e.g. childhood, adolescence, or adulthood.

*S. salivarius* herein can be orally administered in a variety of ways. For example, in the form of compositions discussed above, particularly lozenges, or as suspensions, sustained release formulas (e.g. an oral implant containing the *S. salivarius* strain) or lyophil powders. The *S. salivarius* strains can also be administered by direct application of a lyophil, culture, or cell paste to the oral cavity of the individual. Any mode of administration is suitable as long as the composition is applied to the oral cavity. In one embodiment, the *S. salivarius* or extracts are administered by applying directly to the tongue of the individual, e.g. by brushing.

In general, the amount of *S. salivarius* administered to the individual will be an amount effective for at least partial replacement of one or more halitosis-causing anaerobic bacteria species, or at least black pigmented species, *Eubacterium* and/or *Micromonas* in the oral cavity of the host. "An amount effective for replacement of halitosis-causing anaerobic bacterial strains or at least black pigmented species, *Eubacterium* and/or *Micromonas* in the oral cavity of the host" means an amount effective for oral cavity colonisation by the *S. salivarius* strain, and significant reduction of the resident halitosis-causing anaerobic bacteria (e.g. by competition between the bacteria for nutrients and attachment sites and/or by the production of BLIS by the *S. salivarius* strain). The colonisation by *S. salivarius* may effect short or long term colonisation. Short term colonisation is in the order of up to one month. Long term colonisation means months, or even years.

A significant reduction in anaerobic bacteria in one embodiment may be measured indirectly as a reduction, in an individual's pre-treatment average VSC reading, of 50 ppb, preferably 75 ppb, and more preferably 100 ppb for at least 7 days post-treatment.

The term "unit dose" when used in reference to a composition herein refers to physically discrete units suitable as unitary dosage for the individual, each unit containing a predetermined quantity of active material (viable *S. salivarius* or active extract thereof) calculated to produce the desired therapeutic effect in association with the required diluent, carrier, or excipient.

Specific dosages can vary widely according to various individual variables including size, weight, age, disease severity (e.g. the tenacity and/or number of halitosis-causing resident bacteria) and responsiveness to therapy (e.g. the susceptibility of the individual's oral cavity to colonisation). Methods for determining the appropriate route of administration and dosage may be determined by the consumer as they deem appropriate, or on a case-by-case basis by an attending dentist or other clinician. Such determinations are routine to one of ordinary skill in the art (see for example, *Remington's Pharmaceutical Sciences*, 8th ed., Gennaro, ed., Mack Publishing Company, Easton, Pa., 1990).

In general, the number of *S. salivarius* administered to the individual will range from about $10^2$ to $10^{15}$ bacteria, preferably from about $10^3$ to $10^{14}$ bacteria, more preferably from about $10^5$ to $10^{12}$ bacteria, normally about $10^9$ to $10^{10}$ colony forming units (CFU) per dose. One formulation employs $3.8 \times 10^9$ CFU/lozenge.

Multiple doses of the *S. salivarius* strain can be administered to achieve oral cavity colonisation and replacement of the resident, halitosis-causing strains, particularly black pigmented species, *Eubacterium* and/or *Micromonas* of the individual. The *S. salivarius* strain or extract may need to be administered to the patient once only or more usually repeatedly. Repeat treatments may be once a month, once a week, once a day, twice a day, or as may otherwise be required. Conveniently, the administration may be effected as part of the patient's routine dental care, e.g. as a component of a lozenge, gum, toothpaste, floss, or mouthwash.

To facilitate colonisation, in one embodiment the treatment method of the invention includes a preliminary step of pre-treating the individual to at least reduce the normal microflora present in the oral cavity, including halitosis causing organisms. This pre-treatment comprises the step of administering an antimicrobial agent such as chlorhexidine, chlorine dioxide, triclosan, lactoperoxidase, green tea, or pineapple juice (freeze dried), but not limited thereto. Where a chlorine dioxide mouth rinse is used, it is preferably mixed with water or desirably fruit juice, especially orange juice, prior to administration. The concentration of chlorine dioxide is conveniently between 2,000 and 7,000 ppm, more usually 2,500 to 5,000 ppm, and pH of 3 to 5, preferably 3.5. The pre-treatment may also include physical removal methods such as brushing, flossing and/or tongue scaping, or may follow a prescribed course of antibiotics such as tetracyclines, penicillin, erythromycin, metronidazole, or amoxycillin administered to said individual. *S. salivarius*, or compositions containing same are then administered to the depopulated environment to repopulate same.

One treatment protocol for halitosis comprises pre-treatment by scraping the tongue, brushing teeth and tongue with antibacterial toothpaste (e.g. Perioguard®, 2% chlorhexidine (Colgate, Australia); gargling or rinsing with chlorhexidine (e.g. a rinse with 0.2% chlorhexidine); then taking a lozenge. In a preferred protocol for treatment of halitosis the pre-treatment comprises scraping the tongue and optionally brushing teeth and tongue with a non-chlorhexidene containing toothpaste (e.g. most commercially available toothpastes); gargling or rinsing with chlorine dioxide; then taking a lozenge. In each case, a lozenge is administered 1-4 hours, preferably 2 hours after the pre-treatment. This is followed by administration of a further 2-5, preferably 3 lozenges through the day at intervals of 1-4 hours, preferably about every 2 hours. This protocol is followed for 2-4 days to facilitate colonisation. Usually, in this period the teeth and tongue are brushed and the gargle or rinse continued. However, the brushing with chlorhexidine toothpaste, if used, is discontinued. For maintenance purposes 1, 2, or 3 lozenges, usually 1 to 2 lozenges are taken each day following ordinary tooth brushing. The regime is continued for as long as required.

Successful colonisation of the individual's oral cavity by the *S. salivarius* strain can be established by culturing the bacteria of the individual's oral cavity, and identifying the *S. salivarius* strain by, for example, BLIS production or other methods well known in the art for bacterial strain identification.

Success of treatment can be measured indirectly where post-treatment levels of volatile sulphur compounds are reduced below pre-treatment levels in an individual being treated.

The methods and uses of the invention may further comprise the use of one or more secondary agents, including secondary antibacterial agents as discussed above.

Where the term comprise, comprises, comprised or comprising are used in this specification, they are to be interpreted as specifying the presence of the stated features, integers, steps or components referred to, but not to preclude the presence or addition of one or more other features, integers, steps, components or groups thereof.

All references cited throughout the specification including in the Reference listing are specifically incorporated herein by reference.

Various aspects of the invention will now be illustrated in a non-limiting way by reference to the following experimental section.

EXAMPLES

Deferred Antagonism Test of Anti-Bacterial Activity

The spectrum of inhibitory activity of *Streptococcus salivarius* K12 and K30 was established by use of a deferred antagonism test, essentially as described by Tagg and Bannister (J. Med. Microbiol. 1979; 12:397). In brief, a 1-cm wide diametric streak culture of K12 and K30 (producer strain) was inoculated onto blood agar-calcium medium (Columbia agar base plates, 5% human blood, 0.1% $CaCO_3$ [BDH]). Following incubation in a 5% $CO_2$ atmosphere, for 24 hours at 37° C., the macroscopic cell growth was removed with a glass slide and residual cells on the agar surface were killed by exposure to chloroform vapours for 30 minutes. The agar surface was then aired for 30 minutes. Indicator strains implicated in halitosis which had been grown for 48 hour on blood agar-calcium plates, were suspended in Todd Hewitt broth and used to inoculate at 90-degree angles across the line of the original streak culture with the use of sterile cotton swabs, under anaerobic conditions. After incubation for 48 hours in an anaerobic environment at 37° C. the extent of inhibition of each indicator strain was recorded. The scoring system for the measurement of inhibition was the following: a negative sign (−) denoted no inhibition of the indicator microorganism; a positive symbol (+) indicated that there was some inhibition on the plate where the producer microorganism had grown, but not exclusively over that entire region; two positive symbols (++) denoted that the indicator strain was inhibited where the producer strain was grown; when three positive symbols (+++) were used, growth of the indicator strain was at least 5 mm away from where the producer strain had grown; and four positive symbols (++++) represented inhibition of the indicator strains beyond 5 mm of growth. The results are shown in Table 1 below.

Effect of *S. Salivarius* K12 Extract on Bacteria

*S. salivarius* K12 was grown in skim milk powder broth at 33° C. for 18 h. The bacterial cells were harvested by centrifugation and freeze-dried. One gram of freeze-dried cells were incubated in 10 ml of 95% methanol, pH 2.5 at room temperature for 2 h. The preparation was centrifuged to remove undissolved material. The toxicity of the supernatant was tested using a well diffusion assay.

Inhibition of Black-Pigmented Bacteria (*Prevotella* Species) in Saliva by *S. salivarius* Strains To test the ability of *S. salivarius* against black-pigmented microorganisms which have been implicated in halitosis, *S. salivarius* strains K12 (salA and B producer), NR (salB producer), 20P3 (salA producer) and MU-Neg (non-producer) were swabbed from master plates onto the entire half of several pH-buffered blood plates (Columbia agar base plates, 5% human blood, 0.1% $CaCO_3$ [BDH]). Plates were incubated for 18 hours at 37° C. under 5% $CO_2$ conditions. Bacterial growth by removed using cotton-tipped swabs and chloroform vapours were used to kill any remaining bacteria.

Fifteen millilitres of vancomycin blood agar (per L; 30 g trypticase soy broth [BBL], 15 g agar [BBL] and after autoclaving, 50 ml of defibrinated blood and 10 ml of filter-sterilized vancomycin stock solution [0.014 g in 10 ml $H_2O$]) was overlaid on plates and allowed to set. Fresh saliva-samples from two 'normal' subjects were diluted in sterile saline and 50 ul aliquots were immediately spiral plated on to the prepared agar plates. Plates were incubated under anaerobic conditions at 37° C. for 48-72 hours depending on growth. Both sectors of the plate were counted.

Effect of S. salivarius K12 on Halitosis Subjects

Subjects, Treatment, Probiotic Instillation and Sample Collection

Sixty-five subjects were screened for volatile sulphur compound (VSC) breath readings by halimeter (Interscan Corp., Chatsworth, Calif.). VSC readings in persons with normal breath are typically in the range of 80-150 ppb. At levels of 200-300 ppb oral malodor is noticeable by an observer standing close to the patient. At 350-400 ppb, the odour is noticeable by an observer standing several feet away from the patient. Those subjects with breath scores of greater than 200 ppb on two separate visits were were recruited for the study (n=13). Each signed an Informed Consent under a protocol approved by the Otago Ethics Committee. Subject's upon their second positive visit undertook a mechanical and chemical treatment of their mouths at the laboratory. This consisted of teeth and tongue brushing (2 minutes with Colgate Total™ [0.3% w/v triclosan], Colgate-Palmolive, NY, USA), tongue scraping for 30 seconds, brushing teeth and tongue with a CHX gel (Colgate, Australia) (Perioguard 2.0% CHX mouth gel, 2 minutes) and followed by a 30 second CHX rinse (0.2% CHX, 10% ethanol alcohol). This was followed at intervals by the sucking of a lozenge (BLIS Technologies Limited, Wellington, New Zealand) (commencing 2 hours after treatment and typically 2 hours apart, 4 times daily), each containing >1×10$^9$ colony forming units of streptomycin-resistant S. salivarius K12. On days 2 and 3, subjects brushed their teeth and tongue in the morning with Colgate Total™, used a 30 second CHX rinse (0.2% CHX, 10% ethanol alcohol) and used K12 lozenges as per the first day. The subjects then ceased with the chlorhexidine treatment and took just two lozenges per day on days 4 to 14 after conducting their normal oral care regimen, morning and night.

At each pre-treatment visit and at one and two weeks after treatment initiation the subjects were tested for VSC levels and both saliva samples and tongue swabs were taken (prior to taking morning lozenge). During the study two subjects were sampled more frequently and kept on two lozenges for a period of 28 days. These subjects provided additional samples at day 4, 11, 21, 28 and two weeks post ceasing K12 administration. All measurements were taken in the morning prior to the subjects eating, drinking smoking or using any oral care.

After the study 4 subjects who responded positively to the treatment were followed up six weeks later. To determine the effect of the chlorhexidine treatment on breath scores subjects were asked to repeat the study using the same 3-day CHX regimen, but with no S. salivarius probiotic. As for the study subjects were seen on the seventh day for measurements and samples.

Saliva Analysis

Fresh saliva samples and tongue swabs were tested for N-benzoyl-DL-arginine-2-naphthylamide (BANA) hydrolysis (BANAMet ILC, Ann Arbor, Mich.), since positive scores by the BANA test have previously been associated with the presence of malodour-forming enzyme activities of certain oral bacterial species (1, 3). This was conducted according to the manufacturers' directions. Organoleptic assessment was performed on aliquots of the subjects' frozen saliva specimens. Briefly, 300 ul of thawed saliva was incubated at 37° C. for 10 minutes in a closed eppendorf. After incubation, the lid was removed and the vessel held at approximately 4 cm from the examiner's nose for assessment purposes. The samples were graded according to the same criteria used to assess breath air of halitosis sufferers (7), using a scale of 0-5, with 0 equating to no odour detected and 5 the most severe.

Culture Analysis

Fresh saliva samples were immediately diluted ten-fold in sterile phosphate-buffered saline (PBS, pH 7.5). Fifty-microlitre aliquots were spiral plated onto pH-buffered blood plates (as previously described), Mitis-salivarius agar (Difco, S. salivarius selective) and K12-selective Mitis-salivarius agar containing streptomycin (100 ug/ml, Sigma, Mo., USA). Plates were incubated in a 5% $CO_2$ atmosphere, for 24 hours at 37° C. An estimate of colonisation levels with S. salivarius K12 was obtained from the colony counts on the Mitis-salivarius/streptomycin agar.

Results

Inhibitory Effect

The testing of Streptococcus salivarius strains that were non-producers of salivaricins or that produced either salA and salB, salA only, salB only against some of the bacterial species implicated in halitosis showed that only the gram-positive bacteria were affected when tested by deferred antagonism (Table 1.).

TABLE 1

Sensitivities of selected microoganisms implicated in halitosis to various S. salivarius strains

| | | Inhibition of growth of organisms implicated in halitosis | | | | | | |
|---|---|---|---|---|---|---|---|---|
| S. salivarius strain | Bacteriocin/s produced | Micrococcus luteus I1. | S. anginosus I3. | Eubacterium saburreum ATCC 33271 | Micromonas micros ATCC 33270 | Porphymonas gingivalis ATCC 33277 | Porphymonas gingivalis W50 | Prevotella intermedia ATCC 25611 |
| K12 | Salivaricin $A_2$ Salivaricin B | ++++ | ++++ | ++++ | ++++ | − | − | − |
| K30 | Salivaricin $A_2$ Salivaricin B | ++++ | ++++ | ++++ | ++++ | − | − | − |
| NR | Salivaricin B | ++++ | ++++ | ++ | ++++ | − | − | − |
| 20P3 | Salivaricin A | ++++ | − | ++ | − | − | − | − |
| MU Neg. | Non producer | − | − | − | − | − | − | − |

The maximum amount of inhibition of the gram-positive bacteria was produced by strain K12 and K30, which produces salA and salB. *S. salivarius* strain NR (a salB only producer) had good activity against the Micromonas micros strain but reduced activity against *Eubacterium saburreum* when compared to strain K12 and K30. The non bacteriocin-producing strain (MU Neg.) did not inhibit any of the strains tested.

TABLE 2

Well diffusion assay of *S. salivarius* K12 extract

| | Zone size (mm) | | |
|---|---|---|---|
| Extract | *Micromonas micros* ATCC 33270 | *Prevotella intermedia* ATCC 256111 | *Prevotella intermedia* WS0 |
| *S. salivarius* K12 | 4 | 4 | 4 |

The titre of the *S. salivarius* K12 extract against *Micrococcus luteus* was 128. The extract had activity against Micromonas micros and the two *Prevotella intermedia* strains.

Effect Against Organisms in Saliva

In both subjects the largest reduction (8 and 37% of respective counts) of black-pigmented microorganisms appeared on the control half of the agar plate where K12 (salA, B producer) had grown (Table 2., FIG. 1.).

In both subjects there were substantial reductions (8% and 37% respectively) in the counts of colonies of black-pigmented bacteria on the side of the plate where strain K12 had previously been grown when compared with the counts on the control half of the plate (Table 2., FIG. 1.).

TABLE 2

Effect of *S. salivarius* strains on black-pigmented bacterial counts in saliva specimens

| | *Streptococcus salivarius* strain and numbers of black-pigmented colonies* | | | | | | | |
|---|---|---|---|---|---|---|---|---|
| Subject | K-12 | Control-half | NR | Control-half | 20P3 | Control-half | MU Neg | Control-half |
| A | $1.4 \times 10^5$ | $1.7 \times 10^6$ | $1.4 \times 10^6$ | $3.0 \times 10^6$ | $2.0 \times 10^6$ | $3.5 \times 10^6$ | $1.8 \times 10^6$ | $2.2 \times 10^6$ |
| B | $3.0 \times 10^6$ | $7.9 \times 10^6$ | $4.1 \times 10^6$ | $6.9 \times 10^6$ | $3.1 \times 10^6$ | $6.6 \times 10^6$ | $5.4 \times 10^6$ | $2.6 \times 10^6$ |

*CFU/ml of black-pigmented colony morphology.

There was also some reduction in numbers of black pigmented colonies on the plates on which either the salA only or salB only producers had been grown, but little reduction of numbers on the control plate on which the non-salivaricin producing strain had been grown. Several black pigmented colonies of the type that had been inhibited by the presence of the salivaricins were picked from the control sections of the plates and their DNA was extracted, amplified by PCR and sequenced. The sequencing results (not shown) indicated that the susceptible bacteria had highest homology to *Prevotella* sp. oral clone BE073 (closely related to *Prevotella melaninogenica*) 99% 152 bp (AF385551).

Clinical Data

All subjects completed the two-week study. Volatile sulphur compound (VSC) readings decreased by greater than 100 ppb in 11/13 subjects when measured at 7 days and 8 of these subjects maintained lower than pre-treatment levels when tested again at day 14 (Table 3).

TABLE 3

Subject readings at baseline and after treatment

| | | | Baseline | | | | | | Treatment | | | | |
|---|---|---|---|---|---|---|---|---|---|---|---|---|---|
| | | | Initial Screen | | | Second Visit | | | Day 7 | | | Day 14 | | |
| Demographics | | | | Saliva | | | Saliva | | | Saliva | | | Saliva | |
| Subject (n = 13) | Age | Sex | VSC (ppb) | BANA | organoleptic | VSC (ppb) | BANA | organoleptic | VSC (ppb) | BANA | organoleptic | VSC (ppb) | BANA | organoleptic |
| 4 | 18 | F | 386 | +/− | 3 | 504 | − | ND | 175 | +/− | 2 | 222 | − | 2 |
| 5 | 20 | M | 292 | ND | ND | 394 | ND | ND | 159 | − | 1 | 97 | − | 2 |
| 12 | 18 | M | 404 | + | 3 | 434 | +/− | ND | 59 | +/− | 1 | 364 | − | 2 |

TABLE 3-continued

Subject readings at baseline and after treatment

| | Demographics | | Baseline | | | | | | Treatment | | | | | |
|---|---|---|---|---|---|---|---|---|---|---|---|---|---|---|
| | | | Initial Screen | | | Second Visit | | | Day 7 | | | Day 14 | | |
| | | | | | Saliva | | | Saliva | | | Saliva | | | Saliva |
| Subject (n = 13) | Age | Sex | VSC (ppb) | BANA | organo-leptic | VSC (ppb) | BANA | organo-leptic | VSC (ppb) | BANA | organo-leptic | VSC (ppb) | BANA | organo-leptic |
| 27 | 25 | F | 324 | − | 3 | 514 | − | 3 | 128 | − | 1 | 145 | − | 1 |
| 35 | 39 | M | 320 | − | 4 | 200 | ND | ND | 631 | − | 5 | 413 | +/− | 4 |
| 38 | 69 | M | 363 | +/− | 3 | 290 | + | 3 | 197 | +/− | 2 | 358 | − | 3 |
| 46 | 47 | M | 229 | + | 3 | 327 | + | 4 | 75 | +/− | 2 | 266 | +/− | 4 |
| 47 | 64 | F | 307 | + | 3 | 443 | + | 3 | 126 | +/− | 2 | 183 | +/− | 3 |
| 52 | 68 | M | 486 | + | 4 | 312 | +/− | 3 | 109 | +/− | 3 | 56 | − | 2 |
| 58 | 68 | M | 408 | − | 3 | 213 | +/− | 3 | 154 | +/− | 2 | 122 | − | 1 |
| 59 | 33 | F | 254 | + | 3 | 206 | +/− | 2 | 304 | +/− | 1 | 303 | − | 2 |
| 60 | 41 | M | 433 | +/− | 4 | 381 | − | 3 | 287 | − | 3 | 244 | − | 3 |
| 64 | 43 | M | 286 | + | 3 | 210 | +/− | 2 | 132 | − | 2 | 135 | − | 1 |
| Mean | 42.54 | F = 4 | 345.54 | | 3.25 | 340.62 | | 2.88 | 195.08 | | 2.077 | 223.69 | | 2.307 |
| (SD) | (19.59) | M = 9 | (75.06) | | (0.45) | (113.74) | | (0.60) | (149.26) | | (1.12) | (112.65) | | (1.03) |

+/− = weak positive.
ND = not determined.

The BANA readings were also lower in most subjects post treatment, where no strong positives were detected, whereas several were detected prior. Changes in the organoleptic readings also generally correlated with the other clinical parameters that were measured.

Four subjects who had maintained lower breath readings and parameters during the K12 treatment were recalled six weeks later for monitoring the effect of the chlorhexidine alone. One subject was excluded as their VSC breath levels had not returned to greater than 200 ppb. There was no decrease in the VSC, organoleptic or BANA readings of the three subjects after treatment with CHX only (Table 4.).

TABLE 4

Subject readings of three recalled subjects before and after chlorhexidine

| | Mean VSC (ppb) | Baseline | | | Post CHX treatment | | | VSC |
|---|---|---|---|---|---|---|---|---|
| Subject | change in K12 trial | VSC (ppb) | BANA | Saliva organoleptic | VSC (ppb) | BANA | Saliva organoleptic | (ppb) change after CHX only |
| 27 | −282.5 | 532 | +/− | 2 | 527 | + | 2 | −5 |
| 47 | −220.5 | 298 | +/− | 3 | 244 | +/− | 3 | −54 |
| 60 | −141.5 | 216 | +/− | 3 | 274 | +/− | 2 | +58 |

Culture Data

The average colonisation for the subjects after treatment with *S. salivarius* K12 ranged from 29 to 95 percent. (Table 5)

Generally, there was no significant change in total bacterial counts of the subjects either before or after treatment, however, there was a slight though non-significant increase in *S. salivarius* numbers (Table 5.).

TABLE 5

Mean salivary counts (CFU/ml) of total facultative bacteria, *S. salivarius* and *S. salivarius* K12 in 13 subjects prior to and at 7 and 14 days post initiation of K12 treatment

| | | Pre-treatment* | | Treatment* | |
|---|---|---|---|---|---|
| Bacterial population | Media | Initial screen | Second visit | Day 7 | Day 14 |
| Total | Columbia blood agar calcium | $8.7 \times 10^8$ $(1.4 \times 10^9)$ | $2.4 \times 10^8$ $(2.7 \times 10^8)$ | $3.3 \times 10^8$ $(4.8 \times 10^8)$ | $2.3 \times 10^8$ $(3.7 \times 10^8)$ |

TABLE 5-continued

Mean salivary counts (CFU/ml) of total facultative bacteria,
S. salivarius and S. salivarius K12 in 13 subjects prior to and at
7 and 14 days post initiation of K12 treatment

| Bacterial population | Media | Pre-treatment* | | Treatment* | |
|---|---|---|---|---|---|
| | | Initial screen | Second visit | Day 7 | Day 14 |
| S. salivarius | Mitis salivarius | $4.4 \times 10^7$ ($6.8 \times 10^7$) | $4.5 \times 10^7$ ($6.2 \times 10^7$) | $6.1 \times 10^7$ ($7.8 \times 10^7$) | $6.1 \times 10^7$ ($6.6 \times 10^7$) |
| S. salivarius K12 | Mitis salivarus + streptomycin | 0 | 0 | $1.8 \times 10^7$ ($4.9 \times 10^7$) | $5.8 \times 10^7$ ($1.4 \times 10^7$) |
| Proportion K12 to all S. salivarius | | 0 | 0 | 0.2951 | 0.9508 |

Values in parentheses indicate standard deviation of mean.
*Total and S. salivarius cell counts were not significantly different before or after treatment (Non parametric ANOVA, P > 0.5).

Discussion

Streptococcus salivarius K12 was detectable in each subject's saliva in both post samples taken at least 12 hours after subjects took their last dose the previous night.

When examining the percentage of S. salivarius as a proportion of the total bacterial composition, 85% of the subjects had an increase in the proportion of this bacterium as part of the total count, suggesting that it had become more common in the oral cavity.

The VSC levels of eight subjects were significantly lower when tested one and two weeks after commencing treatment. Three subjects had lower readings only after one week and the remaining two subjects maintained high levels throughout the study. Reduction of BANA activity occurred in most subjects following treatment. In deferred antagonism studies, S. salivarius K12 inhibited gram positive bacterial species implicated in halitosis, and significantly inhibited black-pigmented colony types present in saliva samples.

Based on these studies, the replacement of bacteria implicated in halitosis with a bacteriocin-producing commensal bacterium, particularly S. salivarius K12, appears to provide an alternative therapy for the long term reduction of halitosis.

| | Lozenge |
|---|---|
| Ingredients | Per 945 mg lozenge |
| S. salivarius | $3.8 \times 10^9$ CFU (freeze dried) |
| Isomalt | 600 mg |
| Emdex ™ | 150 mg |
| ProSolv HD ™ | 50 mg |
| Magnesium stearate | 15 mg |
| Flavour | 10 mg |

The ingredients are blended and tablets produced using dry compression.

INDUSTRIAL APPLICATION

BLIS-producing S. salivarius strains, particularly salivaricin B producing strains are active against a number of microorganisms implicated in halitosis (Tables 1, 2 and 6). More particularly, the strains are shown for the first time to be active in a maintenance regime, that is, for generating a cumulative effect against at least some anaerobic halitosis-causing organisms over a period of a week or more. This is surprising where generally S. salivarius strains are thought to be active against only closely related aerobic organisms. Halitosis-causing organisms are anaerobic and occupy niches not generally accessed by S. salivarius, The strains and related active extracts, formulations and compositions herein therefore have application in methods of prophylactically or therapeutically treating individuals against the harmful effects at least of some Eubacterium and Micromonas infections, as well as some black-pigmented colony types, especially in the oral cavity. These methods include treatment of halitosis in which these organisms are the primary causative agents. The S. salivarius extracts and compositions of the invention also have application in the treatment of sore throats.

It will be appreciated that the above description is provided by way of example only and that variations in both the materials and techniques used which are known to those persons skilled in the art are contemplated.

REFERENCES

1. Bosy, A., G. V. Kulkarni, M. Rosenberg, and C. A. McCulloch. 1994. Relationship of oral malodor to periodontitis: evidence of independence in discrete subpopulations. J Periodontol 65:37-46.
2. Burton, J. P., and G. Reid. 2002. Evaluation of the bacterial vaginal flora of 20 postmenopausal women by direct (Nugent score) and molecular (polymerase chain reaction and denaturing gradient gel electrophoresis) techniques. J Infect Dis 186:1770-80.
3. De Boever, E. H., and W. J. Loesche. 1995. Assessing the contribution of anaerobic microflora of the tongue to oral malodor. J Am Dent Assoc 126:1384-93.
4. Kazor, C. E., P. M. Mitchell, A. M. Lee, L. N. Stokes, W. J. Loesche, F. E. Dewhirst, and B. J. Paster. 2003. Diversity of bacterial populations on the tongue dorsa of patients with halitosis and healthy patients. J Clin Microbiol 41:558-63.
5. Tagg, J. R., and L. V. Bannister. 1979. "Fingerprinting" beta-haemolytic streptococci by their production of and sensitivity to bacteriocine-like inhibitors. J Med Microbiol 12:397-411.
6. Walter, J., G. W. Tannock, A. Tilsala-Timisjarvi, S. Rodtong, D. M. Loach, K. Munro, and T. Alatossava. 2000. Detection and identification of gastrointestinal Lactobacillus species by using denaturing gradient gel electrophoresis and species-specific PCR primers. Appl Environ Microbiol 66:297-303.
7. Yaegaki, K., and J. M. Coil. 2000. Examination, classification, and treatment of halitosis; clinical perspectives. J Can Dent Assoc 66:257-61.

The invention claimed is:

1. A method of treating halitosis in an individual in need thereof, the method comprising administering to said individual a BLIS-producing *S. salivarius*, or composition comprising said *S. salivarius*, effective to at least inhibit growth of anaerobic bacteria in the oral cavity of the individual.

2. The method according to claim 1, wherein the anaerobic bacteria are selected from strains of:
 (i) black-pigmented species;
 (ii) Eubacterium; and
 (iii) Micromonas species.

3. The method according to claim 2, wherein the black-pigmented species are Prevotella species.

4. The method according to claim 1, wherein the *S. salivarius* produce one or more of Salivaricin A, Salivaricin $A_1$, Salivaricin $A_2$, Salivaricin B, or variants of any one of these.

5. The method according to claim 4, wherein the *S. salivarius* produces Salivaricin B or a variant thereof.

6. The method according to claim 5, wherein the *S. salivarius* also produces Salivaricin $A_2$ or a variant thereof.

7. The method according to claim 6, wherein the Salivaricin producer is *S. salivarius* strain K12, on deposit at Deutsche Sammlung von Mikroorganismen Und Zellkulturen GmbH, Braunschweig, Germany, accession number DSM 13084.

8. The method according to claim 6, wherein the Salivaricin producer is *S. salivarius* strain K30, on deposit at Deutsche Sammlung von Mikroorganismen Und Zellkulturen GmbH, Braunschweig, Germany, accession number DSM 13085.

9. The method according to claim 1, wherein the composition includes a BLIS-producing *S. salivarius* or an extract thereof, in combination with a diluent, carrier and/or excipient.

10. The method according to claim 9, wherein the composition is an orally administrable composition.

11. The method according to claim 10, wherein the orally administrable composition is formulated as a lozenge, spray, mouth rinse, toothpaste, dentifrice, gargle, capsule, floss, film, chewing gum or chewable tablet.

12. The method according to claim 10, wherein the composition is formulated as a lozenge.

13. The method according to claim 9, wherein the composition is in unit dosage form.

14. The method according to claim 9, wherein the composition further comprises one or more additional antibacterial agents.

15. The method according to claim 14, wherein the additional antibacterial agent(s) are selected from bacteriocin-like inhibitory substance(s) (BLIS).

16. The method according to claim 1, wherein said *S. salivarius*, extract or composition thereof is included in a food, drink, or confectionary.

17. The method according to claim 1, wherein the inhibitory or controlling effect is caused by at least partial colonisation of the oral cavity of an individual with a BLIS-producing *S. salivarius*.

18. The method according to claim 17, wherein the method includes a preliminary step of pre-treating said individual to at least reduce the bacterial population present in the oral cavity.

19. The method according to claim 17, wherein the pre-treatment comprises physical removal of bacteria and/or administration of an antibacterial agent.

20. The method according to claim 19 wherein the antibacterial agent is selected from chlorine dioxide and chlorhexidine.

21. A method of treating halitosis in an individual, the method comprising the steps of:

(i) scraping the tongue of the individual;
(ii) gargling or rinsing with chlorine dioxide; and
(iii) administering to the resulting bacterially depopulated oral cavity an amount of a BLIS-producing *S. salivarius*, or composition comprising said *S. salivarius*, effective to treat said halitosis.

22. The method according to claim 21, which further comprises brushing with a non-chlorhexidine containing toothpaste before gargling or rinsing with chlorine dioxide.

23. The method according to claim 21, wherein the *S. salivarius* or composition is administered in the form of a composition, food, drink or confectionary-comprising a BLIS-producing *S. salivarius* or composition comprising *S. salivarius*.

24. The method according to claim 23, wherein the composition is in the form of a lozenge.

25. The method according to claim 24, wherein lozenges are administered 1 to 5 times a day.

26. The method according to-claim 25, which is repeated daily for 2 to 4 days to facilitate colonisation of the oral cavity of the individual.

27. The method according to claim 26, wherein after colonisation, 1 or 2 lozenges are taken each day following ordinary tooth brushing.

\* \* \* \* \*

SEQUENCE LISTING

<160> NUMBER OF SEQ ID NOS: 8

<210> SEQ ID NO 1
<211> LENGTH: 48
<212> TYPE: PRT
<213> ORGANISM: Salivaricin A

<400> SEQUENCE: 1

Met Lys Asn Ser Lys Asp Ile Leu Asn Asn Ala Ile Glu Glu Val Ser
1               5                   10                  15

Glu Lys Glu Leu Met Glu Val Ala Gly Gly Lys Arg Gly Ser Gly Trp
            20                  25                  30

Ile Ala Thr Ile Thr Asp Asp Cys Pro Asn Ser Val Phe Val Cys Cys
        35                  40                  45

<210> SEQ ID NO 2
<211> LENGTH: 156
<212> TYPE: DNA
<213> ORGANISM: Salivaricin A

<400> SEQUENCE: 2
atgaatgcca tgaaaaactc aaaagatatt ttgaacaatg ctatcgaaga agtttctgaa    60
aaagaactta tggaagtagc tggtggtaaa agaggttcag gttggattgc aactattact   120
gatgactgtc caaactcagt attcgtttgt tgttaa                             156

<210> SEQ ID NO 3
<211> LENGTH: 48
<212> TYPE: PRT
<213> ORGANISM: Salivaricin A1

<400> SEQUENCE: 3

Met Lys Asn Ser Lys Asp Ile Leu Thr Asn Ala Ile Glu Glu Val Ser
1               5                   10                  15

Glu Lys Glu Leu Met Glu Val Ala Gly Gly Lys Lys Gly Ser Gly Trp
            20                  25                  30

Phe Ala Thr Ile Thr Asp Asp Cys Pro Asn Ser Val Phe Val Cys Cys
        35                  40                  45

<210> SEQ ID NO 4
<211> LENGTH: 156
<212> TYPE: DNA
<213> ORGANISM: Salivaricin A1

<400> SEQUENCE: 4
atgagtttta tgaaaaattc aaaggatatt ttgactaatg ctatcgaaga agtttctgaa    60
aaagaactta tggaagtagc tggtggtaaa aaaggttcag gttggtttgc aactattact   120
gatgactgtc cgaactcagt atttgtttgt tgttaa                             156

<210> SEQ ID NO 5
<211> LENGTH: 156
<212> TYPE: DNA
<213> ORGANISM: Salivaricin A2

<400> SEQUENCE: 5
atgattgcca tgaaaaactc aaaagatatt ttgaacaatg ctatcgaaga agtttctgaa    60
aaagaactta tggaagtagc tggtggtaaa agaggtacag gttggtttgc aactattact   120
gatgactgtc caaactcagt attcgtttgt tgttaa                             156

```
<210> SEQ ID NO 6
<211> LENGTH: 51
<212> TYPE: PRT
<213> ORGANISM: Salivaricin A2

<400> SEQUENCE: 6

Met Ile Ala Met Lys Asn Ser Lys Asp Ile Leu Asn Asn Ala Ile Glu
1               5                   10                  15

Glu Val Ser Glu Lys Glu Leu Met Glu Val Ala Gly Gly Lys Arg Gly
            20                  25                  30

Thr Gly Trp Phe Ala Thr Ile Thr Asp Asp Cys Pro Asn Ser Val Phe
        35                  40                  45

Val Cys Cys
    50

<210> SEQ ID NO 7
<211> LENGTH: 114
<212> TYPE: DNA
<213> ORGANISM: Salivaricin B

<400> SEQUENCE: 7
ttgactcttg aagaacttga taacgttctt ggtgctggtg gtggagtaat ccaaaccatt        60
tcacacgaat gtcgtatgaa ctcatggcag ttcttgttta cttgttgctc ttaa            114

<210> SEQ ID NO 8
<211> LENGTH: 37
<212> TYPE: PRT
<213> ORGANISM: Salivaricin B

<400> SEQUENCE: 8

Leu Thr Leu Glu Glu Leu Asp Asn Val Leu Gly Ala Gly Gly Val
1               5                   10                  15

Ile Gln Thr Ile Ser His Glu Cys Arg Met Asn Ser Trp Gln Phe Leu
            20                  25                  30

Phe Thr Cys Cys Ser
            35
```